(12) United States Patent
Pugh et al.

(10) Patent No.: US 10,213,140 B2
(45) Date of Patent: Feb. 26, 2019

(54) OPHTHALMIC LENS WITH A MICROFLUIDIC SYSTEM

(71) Applicant: Johnson & Johnson Vision Care, Inc., Jacksonville, FL (US)

(72) Inventors: Randall B. Pugh, St. Johns, FL (US); Frederick A. Flitsch, New Windsor, NY (US); Karson S. Putt, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 718 days.

(21) Appl. No.: 13/896,708

(22) Filed: May 17, 2013

(65) Prior Publication Data
US 2014/0343387 A1 Nov. 20, 2014

(51) Int. Cl.
| A61B 5/00 | (2006.01) |
| A61B 5/145 | (2006.01) |
| A61B 10/00 | (2006.01) |
| G02C 7/04 | (2006.01) |
| A61F 9/00 | (2006.01) |
| A61F 2/16 | (2006.01) |

(52) U.S. Cl.
CPC ...... *A61B 5/14532* (2013.01); *A61B 5/14507* (2013.01); *A61B 5/6821* (2013.01); *A61B 10/0045* (2013.01); *G02C 7/04* (2013.01); *A61B 5/4839* (2013.01); *A61B 5/7282* (2013.01); *A61B 2010/008* (2013.01); *A61B 2010/0067* (2013.01); *A61F 2/16* (2013.01); *A61F 9/0017* (2013.01); *A61F 2002/1699* (2015.04)

(58) Field of Classification Search
CPC ............ A61B 5/14532; A61B 5/14507; A61B 5/6821; A61B 10/0045; A61B 5/4839; A61B 2010/008; A61B 2010/0067; A61B 5/7282; G02C 7/04; A61F 2002/1699; A61F 9/0017
See application file for complete search history.

(56) References Cited

U.S. PATENT DOCUMENTS

| 6,990,849 B2 | 1/2006 | Bohm et al. |
| 7,701,643 B2 | 4/2010 | Batchko |
| 8,057,041 B2 | 11/2011 | Gruler |

(Continued)

FOREIGN PATENT DOCUMENTS

| WO | WO 2002067688 A8 | 10/2003 |
| WO | WO 2008057238 A2 | 5/2008 |

OTHER PUBLICATIONS

Nanayakkara, et al. "A Fundamental Study on Electrowetting by Traditional and Multifunctional Ionic Liquids: Possible Use in Electrowetting on Dielectric-Based Microfluidic Applications." Analytical Chemistry. Oct. 2008. vol. 80, No. 20. pp. 7690-7698.*

(Continued)

*Primary Examiner* — Tiffany Weston

(57) ABSTRACT

The present invention described a system for an energized ophthalmic device with a media insert that includes microfluidic elements upon or within the media insert. In some embodiments, the microfluidic elements may be useful for the purpose of analyzing an analyte such as glucose in a fluid sample. In addition, some embodiments can function with a medicament administering device to treat an abnormal condition identified during the analyte analysis in the fluid sample.

13 Claims, 13 Drawing Sheets

(56) References Cited

U.S. PATENT DOCUMENTS

| | | | |
|---|---|---|---|
| 8,394,660 B2 | 3/2013 | Kim et al. | |
| 8,608,310 B2 | 11/2013 | Otis et al. | |
| 2003/0006140 A1 | 1/2003 | Vacca et al. | |
| 2003/0179094 A1 | 9/2003 | Abreu | |
| 2005/0118705 A1* | 6/2005 | Rabbitt | B01L 3/502761 |
| | | | 435/287.1 |
| 2006/0155179 A1 | 7/2006 | Muller et al. | |
| 2009/0044875 A1 | 2/2009 | Griss et al. | |
| 2009/0302873 A1 | 12/2009 | Haggett et al. | |
| 2010/0109175 A1* | 5/2010 | Pugh | B29D 11/00028 |
| | | | 264/1.36 |
| 2011/0028807 A1 | 2/2011 | Abreau | |
| 2011/0040161 A1* | 2/2011 | Abreu | A61B 3/1241 |
| | | | 600/321 |
| 2012/0245444 A1 | 9/2012 | Otis et al. | |
| 2014/0192315 A1 | 7/2014 | Liu et al. | |

OTHER PUBLICATIONS

PCT International Search Report for PCT/US2014/037861 dated Sep. 12, 2014.

Gandhi, J., et al., "Emerging Blood Glucose Monitoring Technology in the 21$^{st}$ Century", U.S. Pharmacist, vol. 37, No. 5, (2012) pp. 7-10.

Klonoff, D., "Continuous Glucose Monitoring", Diabetes Care, vol. 28, No. 5, May 2005, pp. 1231-1239.

* cited by examiner

OPHTHALMIC LENS WITH A MICROFLUIDIC SYSTEM

FIELD OF USE

This invention describes a method and system for an Ophthalmic Devices with microfluidic components, and more specifically, the microfluidic components which are capable of performing ocular fluid analysis.

BACKGROUND

Traditionally, an ophthalmic device, such as a contact lens, an intraocular lens, or a punctal plug, included a biocompatible device with a corrective, cosmetic, or therapeutic quality. A contact lens, for example, may provide one or more of vision correcting functionality, cosmetic enhancement, and therapeutic effects. Each function is provided by a physical characteristic of the lens. A design incorporating a refractive quality into a lens may provide a vision corrective function. A pigment incorporated into the lens may provide a cosmetic enhancement. An active agent incorporated into a lens may provide a therapeutic functionality. Such physical characteristics are accomplished without the lens entering into an energized state. An ophthalmic device has traditionally been a passive device.

Novel ophthalmic devices based on energized ophthalmic inserts have recently been described. These devices may use the energization function to power active optical components. For example, a wearable lens may incorporate a lens assembly having an electronically adjustable focus to augment or enhance performance of the eye.

Moreover, as electronic devices continue to be miniaturized, it is becoming increasingly more likely to create wearable or embeddable microelectronic devices for a variety of uses. For example, in one unrelated field, components which include microfluidic regions have become useful tools for diverse purposes. Amongst those purposes, the function of performing the analysis of an analyte in a fluid sample may be possible.

Testing of ocular fluid samples have demonstrated that it contains various chemical constituents that can be useful to identify biomarkers therein. However, the sampling and testing of ocular fluid requires abrasive procedures to the patient and complex equipment. As a result, an ophthalmic device that can incorporate microfluidic elements to perform ocular fluid analytical procedures in convenient and useful ways that are innocuous to a user are desired.

SUMMARY

Accordingly, the foregoing needs are met, to a great extent, by the methods and systems of the present disclosure. In accordance with some embodiments, an ophthalmic device can include a Media Insert with microfluidic analytical systems that can enable small volume fluid sample control.

According to some aspects of the present disclosure, an ocular fluid analysis system for an ophthalmic device can include an energy source capable of energizing the ophthalmic device. The energized ophthalmic device can be suitable to be worn while placed in contact with ocular fluid of a user's eye and includes a microfluidic analytical system in electrical communication with the energy source. Further, the microfluidic analytical system can be configured operatively to measure one or more properties of an ocular fluid sample using a processor capable of executing a program. The program which can include preprogrammed threshold values for one or more of the ocular fluid properties and output a signal when the received measurements are outside the corresponding preprogrammed threshold values.

According to additional aspects of the present disclosure, a method of treating abnormal glucose levels is disclosed. The method which can include: programming glucose biomarkers normal concentrations level thresholds, placing an ophthalmic device in contact with an anterior ocular surface of an eye, obtaining an ocular fluid sample using a microfluidic element of the ophthalmic device, measuring one or more properties of the ocular fluid using one or more sensor components of the ophthalmic device, processing the measurements of the one or more properties of the ocular fluid to determine whether the concentration of glucose biomarkers are within the preprogrammed thresholds, and outputting a signal to a medicament dispensing device based on the measurement. In some embodiments, the method can include the use of an algorithm that is capable of compensating for a time delay in the change of the measured properties to a condition causing the abnormal level.

DETAILED DESCRIPTION OF THE INVENTION

Figures 1A, 1B:
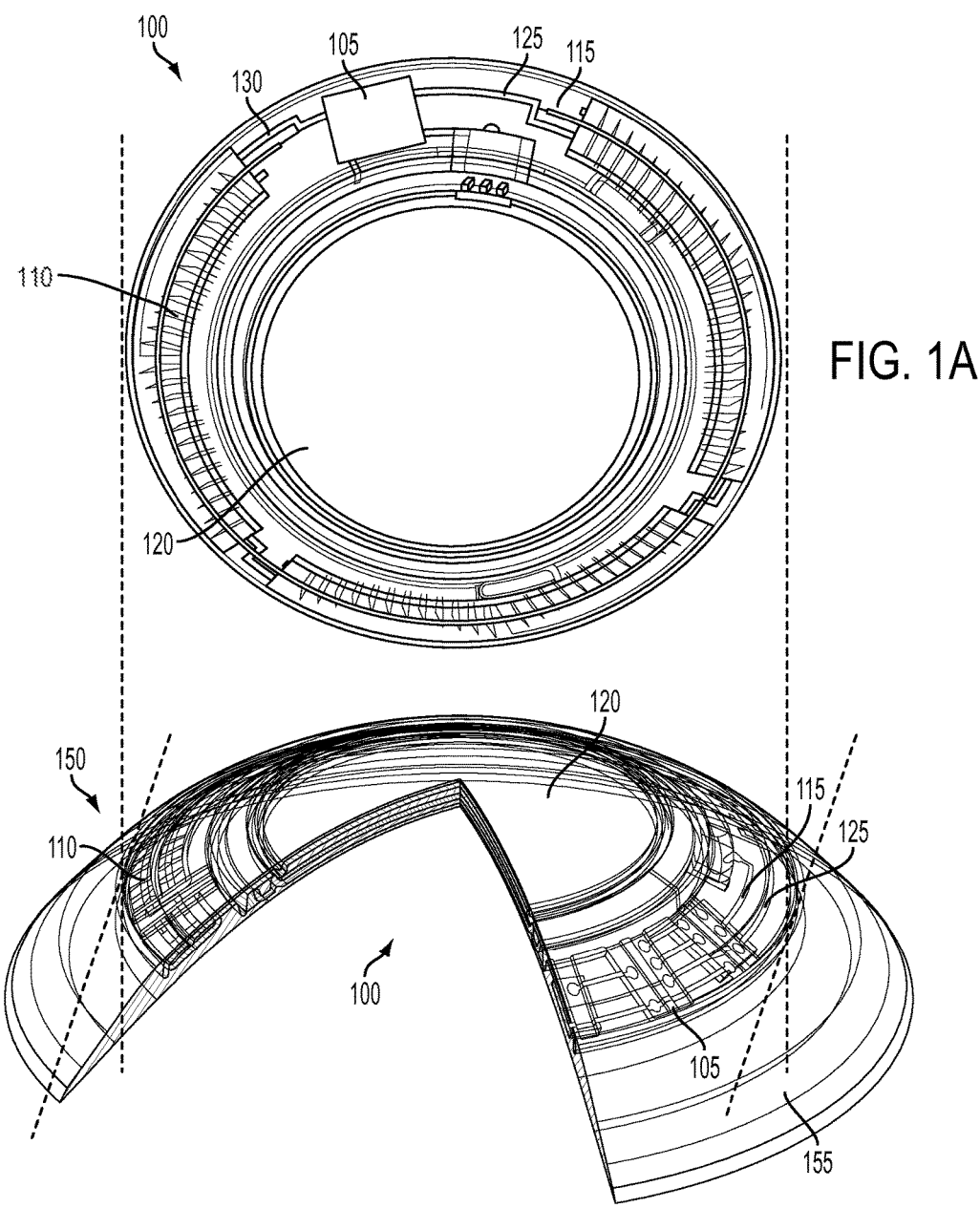
FIG. 1A illustrates a top view of an exemplary Media Insert 100 for an energized ophthalmic device.
FIG. 1B illustrates an isometric view of an exemplary energized Ophthalmic Device 150 with two partial cross sections.

The present invention relates to an ophthalmic device having microfluidic elements and a system that can be used to perform analysis of ocular fluid while in contact with an ocular surface. In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

Glossary

In this description and claims directed to the presented invention, various terms may be used for which the following definitions will apply:

Electro-wetting on Dielectric or EWOD: as used herein refers to a class of devices or a class of portions of devices where a combination of immiscible fluids or liquids, a surface region with defined surface free energy and an electro-potential field are present. Typically, the electro-potential field will alter the surface free energy of the surface region, which may alter the interaction of the immiscible fluids with the surface region.

Energized: as used herein refers to the state of being able to supply electrical current to or to have electrical energy stored within.

Energy: as used herein refers to the capacity of a physical system to do work. Many uses within this invention may relate to the said capacity being able to perform electrical actions in doing work.

Energy Source: as used herein refers to a device or layer that is capable of supplying Energy or placing a logical or electrical device in an Energized state.

Energy Harvester: as used herein refers to a device capable of extracting energy from the environment and converting it to electrical energy.

Functionalized: as used herein refers to making a layer or device able to perform a function including for example, energization, activation, or control.

Leakage: as used herein refers to unwanted loss of energy.

Lens or Ophthalmic Device: as used herein refers to any device that resides in or on the eye. These devices may provide optical correction, may be cosmetic, or may provide functionality unrelated to the eye. For example, the term lens may refer to a contact lens, intraocular lens, overlay lens, ocular insert, optical insert, or other similar device through which vision is corrected or modified, or through which eye physiology is cosmetically enhanced (e.g. iris color) without impeding vision. Alternatively, the Lens may provide non-optic functions such as, for example, monitoring glucose or administrating medicine. In some embodiments, the preferred lenses of the invention are soft contact lenses are made from silicone elastomers or hydrogels, which include, for example, silicone hydrogels, and fluorohydrogels.

Lithium on Cell: as used herein refers to an electrochemical cell where Lithium ions move through the cell to generate electrical energy. This electrochemical cell, typically called a battery, may be reenergized or recharged in its typical forms.

Media Insert: as used herein refers to an encapsulated insert that will be included in an energized ophthalmic device. The energization elements and circuitry may be incorporated in the Media Insert. The Media Insert defines the primary purpose of the energized ophthalmic device. For example, in embodiments where the energized ophthalmic device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose or administering medicine.

Microfluidic Analytical Systems: as used herein can refer to a low energy consumption system including one or more pore(s) from which a fluid sample may be collected from, and in some embodiments, moved through a channel or diffused, for the characterization of one or more properties of the fluid sample. In some embodiments, the Microfluidic Analytical Systems can include active microfluidic components, such as micro-pumps and micro-valves. Alternatively or additionally, in some embodiments, droplets may be controlled, for example, using electrowetting and/or electrophoresis techniques.

Operating Mode: as used herein refers to a high current draw state where the current over a circuit allows the device to perform its primary energized function.

Optical Zone: as used herein refers to an area of an ophthalmic lens through which a wearer of the ophthalmic lens sees.

Power: as used herein refers to work done or energy transferred per unit of time.

Rechargeable or Re-energizable: as used herein refers to a capability of being restored to a state with higher capacity to do work. Many uses within this invention may relate to the capability of being restored with the ability to flow electrical current at a certain rate and for a certain, reestablished period.

Reenergize or Recharge: as used herein refers to restoring to a state with higher capacity to do work. Many uses within this invention may relate to restoring a device to the capability to flow electrical current at a certain rate and for a certain, reestablished period.

Reference: as use herein refers to a circuit which produces an, ideally, fixed and stable voltage or current output suitable for use in other circuits. A reference may be derived from a bandgap, may be compensated for temperature, supply, and process variation, and may be tailored specifically to a particular application-specific integrated circuit (ASIC).

Reset Function: as used herein refers to a self-triggering algorithmic mechanism to set a circuit to a specific predetermined state, including, for example, logic state or an energization state. A Reset Function may include, for example, a power-on reset circuit, which may work in conjunction with the Switching Mechanism to ensure proper bring-up of the chip, both on initial connection to the power source and on wakeup from Storage Mode.

Sleep Mode or Standby Mode: as used herein refers to a low current draw state of an energized device after the Switching Mechanism has been closed that allows for energy conservation when Operating Mode is not required.

Stacked: as used herein means to place at least two component layers in proximity to each other such that at least a portion of one surface of one of the layers contacts a first surface of a second layer. In some embodiments, a film, whether for adhesion or other functions may reside between the two layers that are in contact with each other through said film.

Stacked Integrated Component Devices or SIC Devices: as used herein refers to the products of packaging technologies that assemble thin layers of substrates that may contain electrical and electromechanical devices into operative-integrated devices by means of stacking at least a portion of each layer upon each other. The layers may comprise component devices of various types, materials, shapes, and sizes. Furthermore, the layers may be made of various device production technologies to fit and assume various contours.

Storage Mode: as used herein refers to a state of a system comprising electronic components where a power source is supplying or is required to supply a minimal designed load current. This term is not interchangeable with Standby Mode.

Substrate Insert: as used herein refers to a formable or rigid substrate capable of supporting an Energy Source within an ophthalmic lens. In some embodiments, the Substrate insert also supports one or more components.

Switching Mechanism: as used herein refers to a component integrated with the circuit providing various levels of resistance that may be responsive to an outside stimulus, which is independent of the ophthalmic device.

Energized Ophthalmic Device

Proceeding to FIG. 1A, a top view of an exemplary Media Insert 100 for an energized ophthalmic device is depicted. The Media Insert 100 may comprise an Optical Zone 120 that may or may not be functional to provide vision correction. Where the energized function of the ophthalmic device is unrelated to vision, the Optical Zone 120 of the Media Insert 100 may be void of material. In some embodiments, the Media Insert 100 may include a portion not in the Optical Zone 120 comprising a substrate 115 incorporated with energization elements 110 and electronic components 105.

In some embodiments, a power source 110, which may be, for example, a battery, and a load 105, which may be, for example, a semiconductor die, may be attached to the substrate 115. Conductive traces 125 and 130 may electrically interconnect the electronic components 105 and the energization elements 110. In some embodiments, the Media Insert 100 can be fully encapsulated to protect and contain the energization elements 110, traces 125 and 130, and electronic components 105. In some embodiments, the encapsulating material may be semi-permeable, for example, to prevent specific substances, such as water, from entering the Media Insert 100 and to allow specific substances, such as ambient gasses, fluid samples, and/or the byproducts of reactions within energization elements 110, to penetrate and/or escape from the Media Insert 100.

Referring now to FIG. 1B, an isometric view of an exemplary energized Ophthalmic Device 150 with two partial cross sections is depicted. In some embodiments, the Media Insert 100 may be included in/or an Ophthalmic Device 150, which may comprise a polymeric biocompatible material. The Ophthalmic Device 150 may include a rigid center, soft skirt design wherein a central rigid optical element comprises the Media Insert 100. In some specific embodiments, the Media Insert 100 may be in direct contact with the atmosphere and the corneal surface on respective anterior and posterior surfaces, or alternatively, the Media Insert 100 may be encapsulated in the Ophthalmic Device 150. The periphery 155 of the Ophthalmic Device 150 may be a soft skirt material, including, for example, a hydrogel material. The infrastructure of the Media Insert 100 and the Ophthalmic Device 150 can provide an environment to perform analysis of ocular fluid while in contact with an ocular surface according to aspects of the present invention. Ocular fluid samples can include any one, or a combination of: tear fluid, aqueous humour, vitreous humour, and other interstitial fluids located in the eye.

Figure 2:
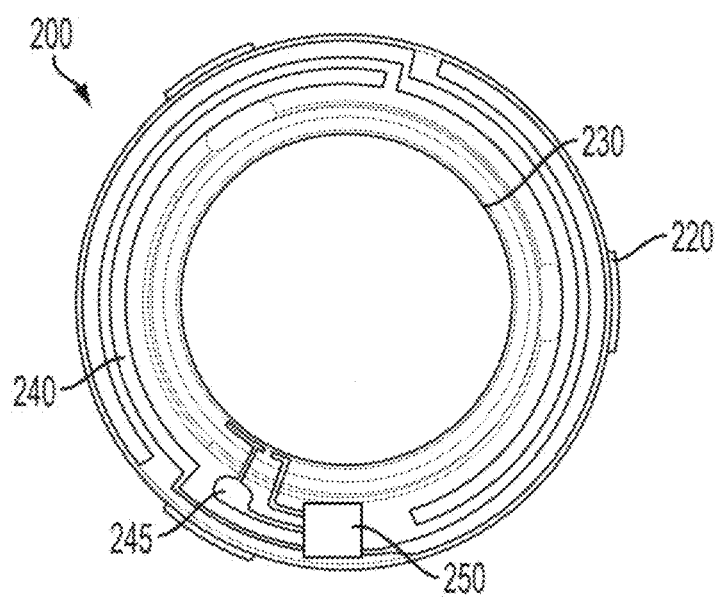
FIG. 2 illustrates a top view of an exemplary multi-piece annular shaped form insert 200.

Referring now to FIG. 2A, a top view of an exemplary multi-piece annular shaped insert 200 is depicted. As depicted, the exemplary multi-piece annular shaped insert 200 may be a ring of material around a central optical zone that is devoid of material. Moreover, the annular shaped insert 200 may be defined by an exterior extent 220 and an internal annulus edge 230. Included in between the exterior extend 220 and the internal annulus edge 230 may be found energization elements 240, interconnect features 245 of various types and/or an electronic circuit element 250.

In some embodiments, the front insert piece and the rear insert piece may be joined and sealed together. In different embodiments, other structural features and means can be implemented to join both pieces together. Also in an encapsulated location may be an integrated circuit element connected to interconnection elements.

In other embodiments, a different type of structure may be found. A gap or pore may be formed to allow some portion of the interior of the annular shaped insert to be open to an external environment. There may be numerous components that may connect to this opening, and can themselves be encapsulated within the annular shaped insert. Accordingly, this ability to allow component(s) to be situated within the annular shaped insert to controllably interface with fluids and/or gasses in their exterior environment can, in some embodiments, enable for the incorporation of microfluidic elements within ophthalmic device.

Microfluidic Elements for Analyte Analysis

Figure 3:
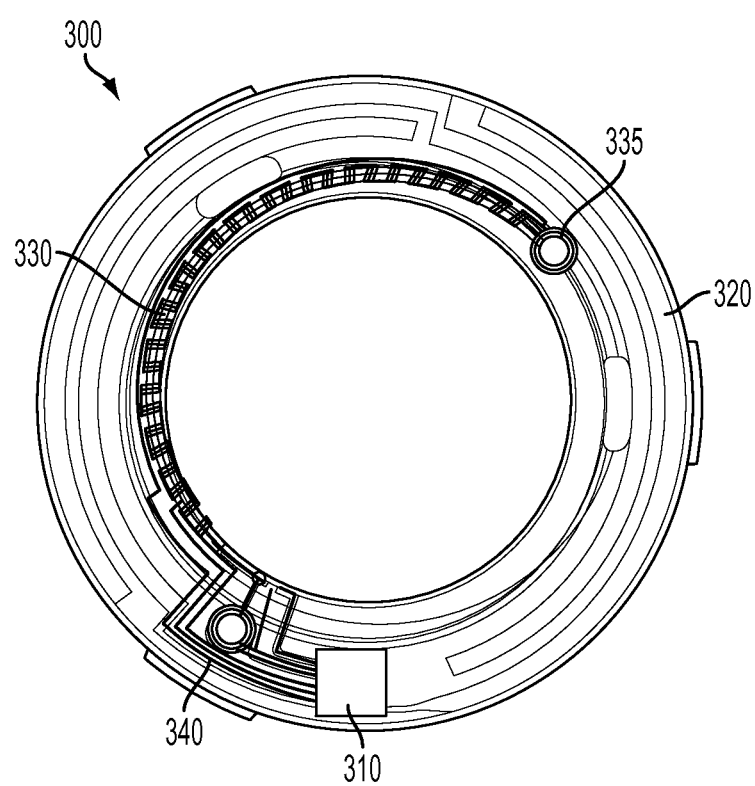
FIG. 3 illustrates a top view of an exemplary Microfluidic Analytical System 300 of an ophthalmic device.

Referring now to FIG. 3, a top view of an exemplary Microfluidic Analytical System 300 of an ophthalmic device is depicted upon an ophthalmic Media Insert. In addition to energization elements 320, control circuitry 310, and interconnect features 340, in some embodiments, the Media Insert can include a Microfluidic Analytical System 300 including a waste fluid retention component 335. The Microfluidic Analytical System 300 may be capable of determining an analyte/biomarker, in terms of its presence or its concentration, in a fluid sample.

Figure 4:
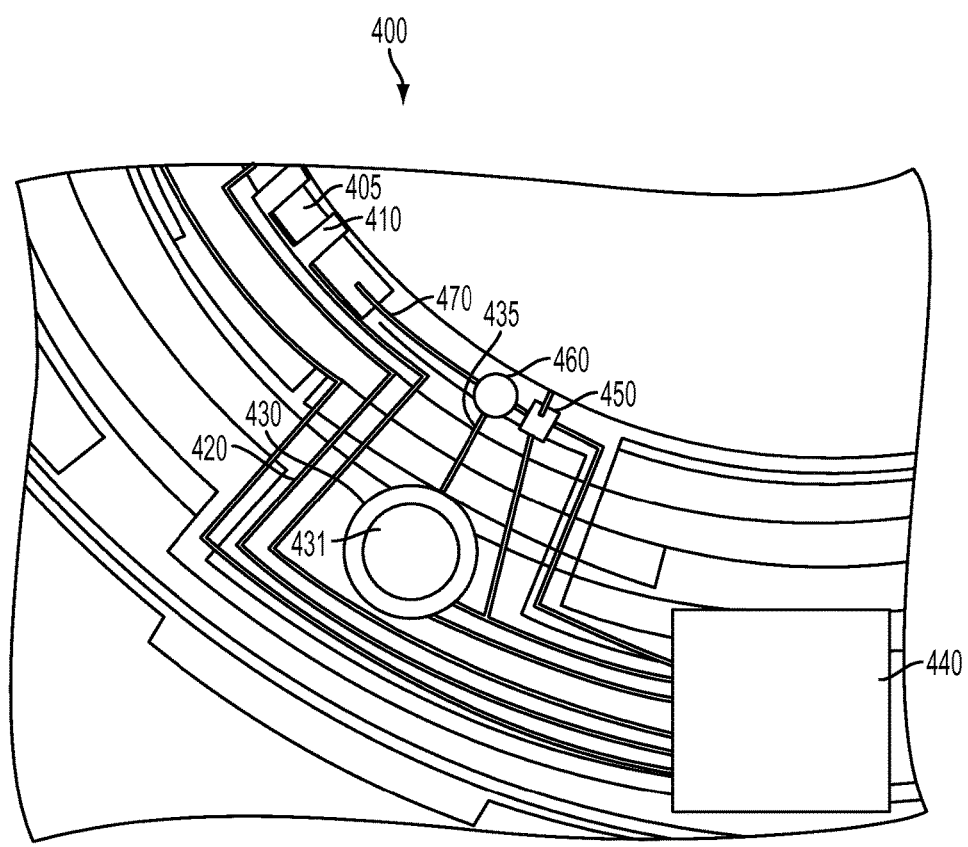
FIG. 4 illustrates a magnified top view partial section of the Microfluidic Analytical System 300 of FIG. 3 with an exemplary pumping mechanism 400 as well as sampling regions and controlling components.

Referring now to FIG. 4, a magnified top view partial section of the Microfluidic Analytical System 300 of FIG. 3 with an exemplary pumping mechanism 400 as well as sampling regions and controlling components is depicted. As shown, in some embodiments control circuitry 440 may be electrically connected to components of the microfluidic analytical system through interconnect(s) 420. A control element 450 for a pore (not shown) may be included and be useful for connecting the Microfluidic Analytical System 300 to fluid (not shown) outside of the insert. Exemplary aspects of different designs of pores may be found in following sections; however, the pore may allow fluid samples to be passed from outside the insert environment to a pumping element 460.

In some embodiments, the pumping element 460 may have an activating or driving component 430 that can be capable of engaging the pump 460. In one example, the pump element 460 may comprise a flexible and collapsible membrane that may be activated by the application of pressure upon the membrane. There may be numerous manners for driving the application of pressure upon the membrane. For example, a fluid may fill a cavity 431 and flow through a tube 435 connecting the cavity 431 to the pumping element 460. Accordingly, the cavity 431 may include features allowing the application of pressure upon the fluid contained within. For example, piezoelectric components may be used to expand volume on the application of voltage thus pressurizing the contained fluid. In other embodiments, thermo-compressive materials may respond to a temperature change that may be controlled by the application of electric energy to a heating element. In a yet another embodiment, an Electrowetting on Dielectric (EWOD) component may exert a pressure on the fluid by a change in the wetting characteristics of a surface in cavity 431 upon the application of a potential. There may also be other means of driving a pump mechanism that may also be directly engaged at the pump element 460 itself. Still further diversity may derive from the use of EWOD components to influence the flow of fluids themselves rather than the use of mechanical pumping means.

The pump element 460 may force fluid to flow through a channel 470 and subsequently into an analyzing chamber 405 of the Microfluidic Analytical System 400. Further detail of the components in such chambers 405 will be described in following sections, but briefly stated the fluid may flow through the analyzing chamber 405 and cause influences to occur on electrode(s) 410 which may be part of the components.

Figure 5:
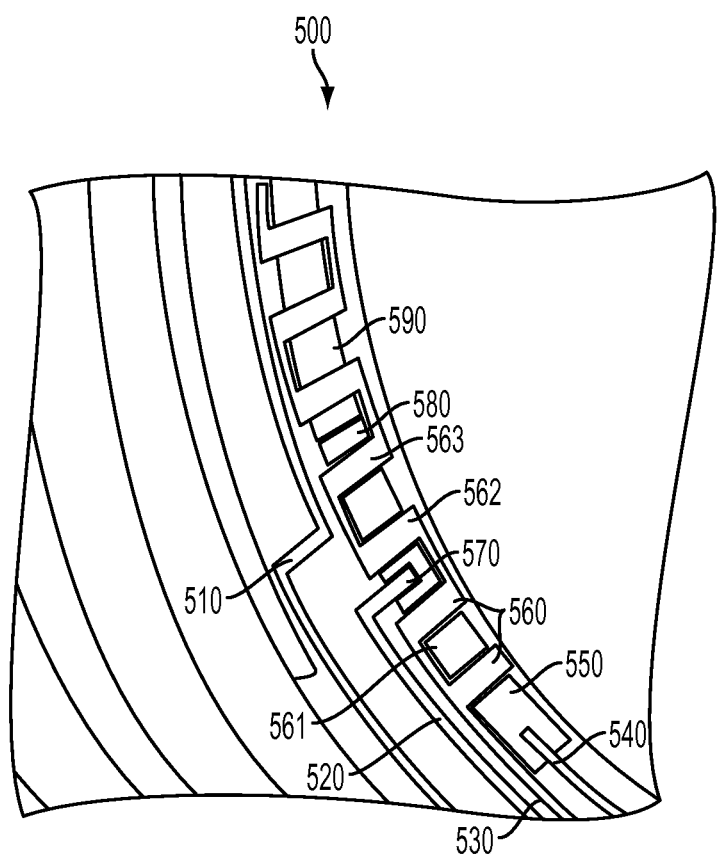
FIG. 5 illustrates a top view partial section of an exemplary Microfluidic Analytical System 500 with a fluid sample being flowed through the microfluidic analysis component.

Referring now to FIG. 5, a top view partial section of an exemplary Microfluidic Analytical System 500 with a fluid sample being flowed through the microfluidic analysis component is illustrated. Because of the nature of an annular system, the components may be observed to be deployed in a curvilinear fashion as there may be numerous details that change in a curvilinear system including, for example, the exact shapes of electrodes and chamber cross sections. In other embodiments, however, linear analytical systems may be formed that have dimensions that allow them to fit in the ocular environment. Further, in additional embodiments, regardless of the nature of the system along the analysis chamber, the entire substrate that the chamber rests upon can be curved allowing it to rest upon the roughly spherical surface of an eye. The details of the three dimensional nature of the analysis chamber may factor into models related to the performance of the systems. For illustration purposes, however, this description declares these nuances, but will illustrate an exemplary embodiment by curving the features of a linear Microfluidic Analytical System 500.

Depicted in the portion of the Microfluidic Analytical System 500, a micro-channel 550 for receiving and transporting fluid samples is shown. These fluid samples may be pumped, for example, by the previously discussed pumping system (e.g. 460 in FIG. 4) from an external location. For example, fluid samples may be sampled from ocular fluid that may surround a contact lens containing the Microfluidic Analytic System 500. An analyte sensor 570 may be found for example along the micro-channel. This analyte sensor 570 may be capable of performing one or more of: an electrochemical analysis step, a photometric analysis step or other analytical steps upon fluid samples. In an exemplary embodiment, the analysis step may relate to a photometric sensing of glucose concentration based on a fluorescence sensor typology using one or more components. In another example, the sensor may detect the presence of reaction products from a glucose oxidase interaction with portions of the analyte sensor 570 and the fluid sample. There may be numerous electrical interconnections 520 which connect the sensing element 570 to control electronics.

Fluid may flow into the micro-channel 550 from a pump channel 540. As the fluid flows into the micro-channel it may displace other fluid in a particular region, or on an initial use may displace ambient gas in the channel. As a fluid flows, it may be sensed by a pre-sensor micro-channel portion comprising electrodes 560 and 561 as well as a post-sensor portion comprising electrodes 562 and 563, In some embodiments the measurement of impedance between electrodes such as 560 and 561 may be used to sense the flow of material. In other embodiments, the resistance of a chain of electrodes 562 and 563 may be altered by the presence of a fluid within the micro-channel 550, or the presence of a front between two fluids of different characteristics residing in the micro-channel 550. A fluid 580 may flow through the micro-channel from an empty region of the micro-channel 590 to be sampled. Alternatively, micro-channel portion at 590 may represent a different solution of fluid that may for example have different concentration of electrolytes, and therefore, conductivity than that of typical tear fluid.

In general, measuring impedances, or ohmic resistances, between position electrodes 560-563 in embodiments of the present invention can be accomplished by applying a voltage therebetween and measuring the resulting current. Either a constant voltage or an alternating voltage can be applied between the position electrodes 560-563 and the resulting direct current (DC) or alternating current (AC), respectively, measured. The resulting DC or AC current can then be used to calculate the impedance or ohmic resistance. Furthermore, one skilled in the art will recognize that measuring impedance can involve measuring both an ohmic drop (i.e., resistance [R] in Ohms or voltage/current) and measuring capacitance (i.e., capacitance in Farads or coulombs/volt). In practice, impedance can be measured, for example, by applying an alternating current to the position electrode(s) 560-563 and measuring the resulting current. At different frequencies of alternating current, either resistive or capacitive effects prevail in determining the measured impedance. The pure resistive component can prevail at lower frequencies while the pure capacitive component can prevail at higher frequencies. To distinguish between the resistive and capacitive components, the phase difference between the applied alternating current and the measured resulting current can be determined. If there is zero phase shift, the pure resistive component is prevailing. If the phase shift indicates that the current lags the voltage, then the capacitive component is significant. Therefore, depending on the frequency of an applied alternating current and position electrode configuration, it can be beneficial to measure either resistance or a combination of resistance and capacitance.

Referring back to the specific example of FIG. 5, impedance measurements can be performed by, for example, applying an alternating voltage between first position electrode 530 and a final position electrode connection 510 and measuring the resulting alternating current. Since the chain of electrodes including 560, 561, 562 and 563 can be a portion of a capacitor, (along with any substance [e.g., air or a liquid sample] within micro-channel 550 between subsequent position electrodes and any layers that may be separating the position electrodes from direct contact with the fluid in the micro-channel 550), the measured current can be used to calculate the impedance. The presence or absence of a liquid sample in micro-channel 550, 590 between electrodes will affect the measured current and impedance. The frequency and amplitude of the alternating voltage applied between a first and second position electrodes 560-563 can be predetermined such that the presence of a liquid sample between a first and second position electrodes 560-563 can be detected by a significant increase in measured current.

With respect to the measurement of impedance or resistance, the magnitude of the applied voltage can be, for example, in range from about 10 mV to about 2 volts for the circumstance of an ophthalmic tear fluid sample and carbon-based or silver-based ink position electrodes. The lower and upper limits of the applied voltage range are dependent on the onset of electrolysis or electrochemical decomposition of the liquid sample. In instances where an alternating voltage is employed, the alternating voltage can be applied, for example, at a frequency that results in a negligible net change in the liquid sample's properties due to one or more electrochemical reaction. Such a frequency range can be, for example, from about 10 Hz to about 100 kHz with a voltage waveform symmetrical around 0 Volts (i.e., the RMS value of the alternating voltage is approximately zero).

As depicted, analyte sensor 570 and position electrodes 560-563 can each be in operative communication with the micro-channel 550. It should be noted that position electrodes 560-563 employed in embodiments of the present invention can be formed of any suitable conductive material known to those skilled in the art, including conductive materials conventionally used as analytical electrode materials and, in particular, conductive materials known as suitable for use in flexible circuits, photolithographic manufacturing techniques, screen printing techniques and flexo-printing techniques. Suitable conductive materials include, for example, carbon, noble metals (e.g., gold, platinum and palladium), noble metal alloys, conductive potential-forming metal oxides and metal salts. Position electrodes can be formed, for example, from conductive silver ink, such as the commercially available conductive silver ink Electrodag 418 SS.

Figure 6:
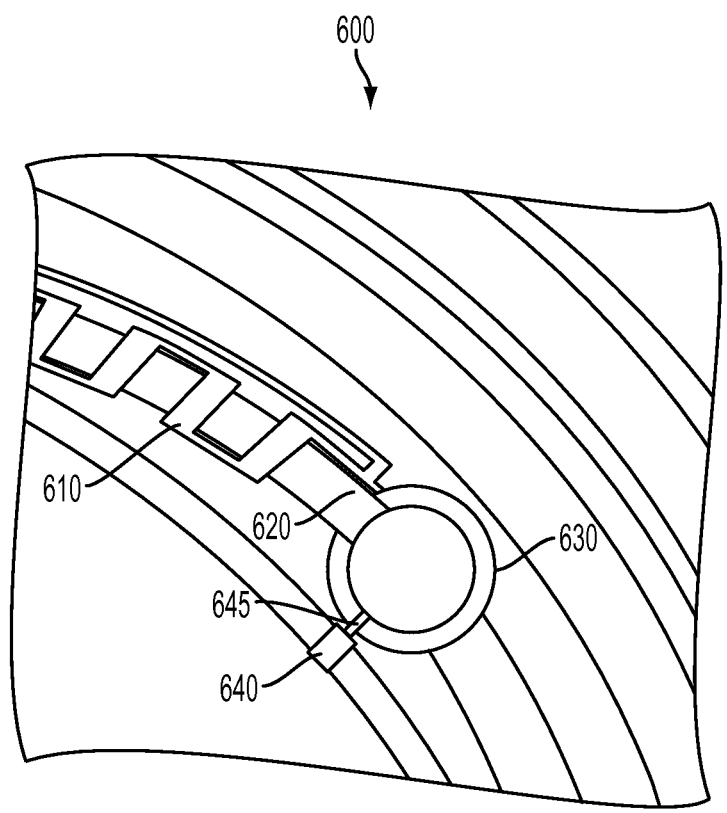
FIG. 6 illustrates a top view section of an exemplary Microfluidic Analytical System component 600 with a waste storage element 630.

Referring now to FIG. 6, a top view section of an exemplary Microfluidic Analytical System component 600 with a waste storage element 630 is depicted. In the exemplary embodiments, electrode 610 for measuring the flow rate of fluid in the system may be an end electrode of many others (not depicted in FIG. 6). Fluid may flow through the micro-channel 620 and continue to a fluid retention vessel 630. The fluid rentention vessel may be used, for example, for higher volume of fluid analysis therein. In some embodiments, a pore 640 can include a pore control element 645 for connecting the fluid retention vessel 630, which may be also be used as a waste storage element, 630 to regions located external to the insert. In addition, in some embodiments the pore control element 645 connection may be useful for equalizing gas pressure as the microfluidic components fill with fluid. In other embodiments, the pore 640 and pore control element 645 may be useful for emitting fluid from the ophthalmic device. The pore 640 may also be useful for connecting an end of the Microfluidic Analytical System to its external region in an eye environment, which can allow for continuous monitoring without the removal of the ophthalmic device. In other embodiments, the pore 640 and pore control element 645 may be useful for flow control through the Microfluidic Analytical System in a storage location, such as the fluid retention vessel 630. For example, while in storage, the Microfluidic Analytical System may be cleansed or refreshed by the flowing of solutions through the system and, in some embodiments, subjected to calibration protocols. Control of these functions may be performed by the integrated circuit components within the lens which may also be in communication with external controlling systems.

Energized Ophthalmic Devices with Lab on a Chip Components

Figure 7:
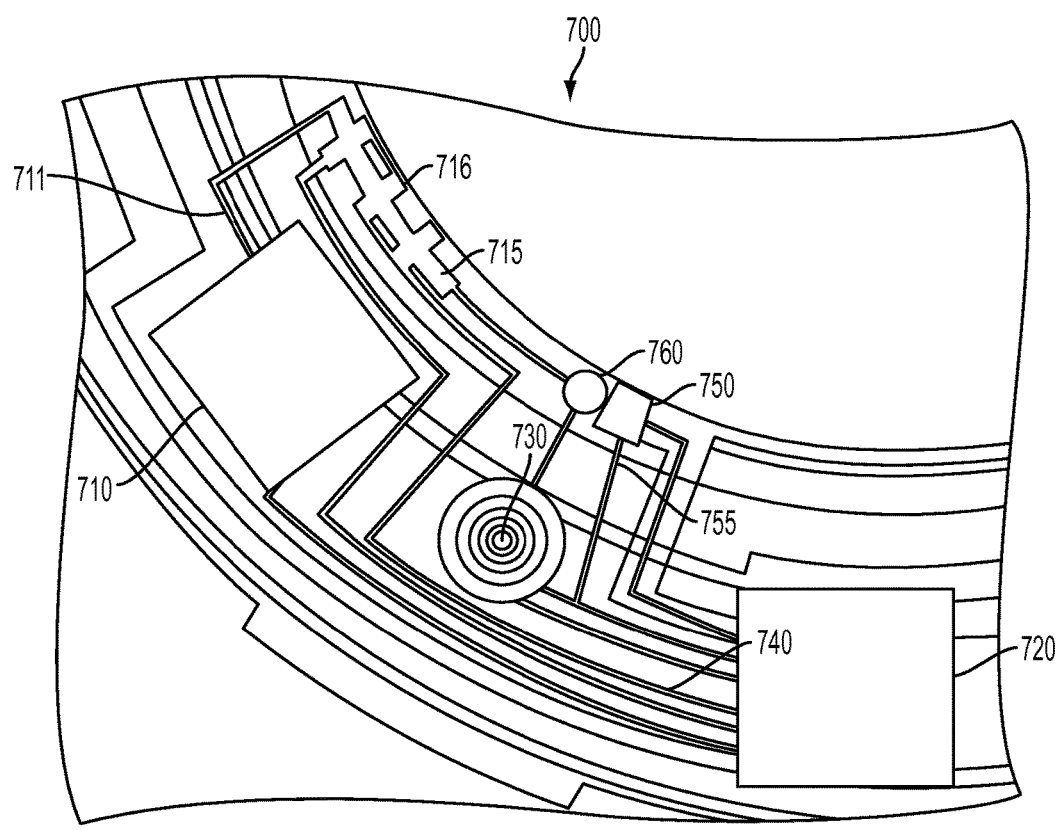
FIG. 7 illustrates a top view section of an exemplary pumping mechanism 700 for a Microfluidic Analytical System using lab on a chip components.

Referring now to FIG. 7, a top view section of an exemplary pumping mechanism 700 for a Microfluidic Analystical System using lab on a chip component 710 is depicted. A lab on a chip component 710 may share many aspects with the embodiment of the Microfluidic Analytical System that has been previously discussed. Similarly, however, in some embodiments small droplets may be moved around within the lab on a chip 710 not through the action of a pump 760 but by control of the droplets with EWOD components. Droplets may be combined in elements of the lab on a chip component 710 to perform chemical processing. Numerous analysis techniques that may be performed. For example, in some embodiments the analysis of glucose as an analyte may be performed. The technique for this analysis may include, for example, an electrochemical or photometric technique as described or other techniques that may relate to the mixing of chemical substances that may be initially stored in the lab on a chip component 710.

Various components such as energization elements (not shown), interconnects 740, and sealing aspects previously described may take place in the annular Media Insert piece of the present example. Further, an electronic circuit 720 capable of controlling various components including a lab on a chip component 710 can be implemented. A pore 750 and a pore control system 755 may control the sampling of fluid samples from the ophthalmic device environment. A pump actuator 730 may actuate a pump 760 which may be mechanical in nature such as a membrane based pump. Droplets of a fluid sample may be pumped into micro-channel 715 for metering of the volume and sample flow rate through the use of electrodes such as electrode 716 as described in the present disclosure. The droplets may be provided to the lab on a chip component 710 through a channel 711 where it may be further processed. The lab on a chip component 710 may use the pumped action on the sample to control flow within itself, or in other embodiments, it may control the flow rate of the sample provided to it on its own.

In additional embodiments, the lab on a chip component 710 may be able to sense fluid in its environment without the need of an external pumping systems. However, a pore such as item 750 can still be useful to provide control over flow of external fluid into the environment of the lab on a chip component. Thereafter the lab on a chip component 710 may sample the introduced sample on its own, for example, by the control through electrowetting on dielectric or electrophoresis features that can attract and move fluid samples.

The lab on a chip component 710 may comprise a design that can be consistent with the present description including, for example, very thin lab on chip flexible components to allow for the deformation into a shape consistent with the three dimensional shape of an ocular surface. In some embodiments, the shape and thickness of the lab on a chip component 710 may allow it to be included in a planar form within the ophthalmic insert device.

Energized Pumping Systems for Microfluidic Components

Figure 8:
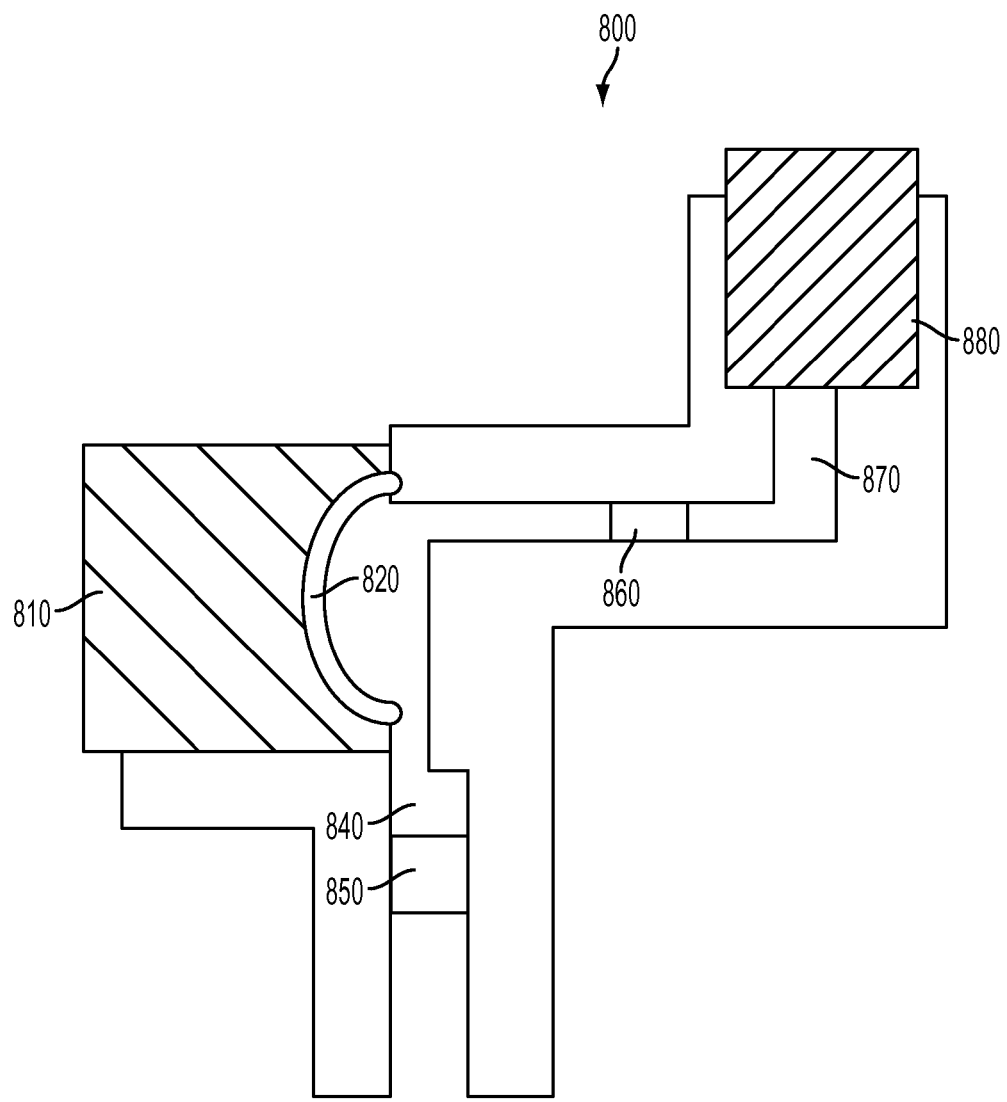
FIG. 8 illustrates a schematic design of an exemplary pumping system 800 that may be useful for implementing aspects of the disclosure.

Referring now to FIG. 8, a schematic design of an exemplary pumping system 800 that may be useful for implementing aspects of the disclosure is depicted. As previously mentioned, in some embodiments it is useful to provide a means of pumping fluid samples both in and out of an ophthalmic device and also within components located inside an ophthalmic device. In the present example, pumping system 800 may have an inlet for fluid samples with a flow controlling system 880. When fluid is allowed to flow by flow controlling system 880 it can proceed through a channel 870. A membrane component 820 may be included so that when deflected by a force upon it, it can cause gas and/or liquid fluids to be compressed and act to pump them.

In some embodiments, the membrane component 820 may be located on a fluid path 840 between a system of check valves 850 and 860, which may be included in the pumping system 800 to ensure the flow in a preferred direction. In other embodiments, the design and geometry of the flow regions may effect a preferred flow condition. For example, as fluid is compressed in flow path region 840, which is a continuation of a flow path region 870, liquid sample can flow towards other regions of the Microfluidic Analytic System.

A force upon a surface of the membrane component 820 can cause actuation of the pumping system 800. The force may be applied, for example, by an active component 810 that can provide the deflection. In some embodiments a fluid may be capable of providing the force for deflection. Through the use of hydraulic principles, for example a larger volume of fluid may be concentrated down to match up with the surface of the membrane component 820. In these types of embodiments, elements that pressurize the larger volume fluid may perform the required task. Mechanical piston activation where electrostatic or magnetostatic forces are used may also be included in some embodiments. Also, thermal expansion and electrically (Piezoelectric) activated expansion of materials that surround the fluid may also be used to provide a means of pressurizing the fluid. For example, in some embodiments, Electrowetting on dielectrics may be employed to pressurize the fluid. A chamber 810 may be formed to have a surface treatment that under the lack of an electric potential favors the attraction of the fluid included in the chamber 810. With an electrode (not shown) in contact with the fluid and another beneath the treated surface, a potential field may be established across the surface region. As the wetting of the region is changed by the application of the potential field, the fluid may become pressurized and with a hydraulic concentration, the resulting pressure on the membrane component 820 may deflect it and effect a pumping stroke. By reducing the potential field, the effect may be reversed on the hydraulic fluid with the result being a relaxation of the membrane component 820 and the completion of a pumping cycle.

Other numerous means for pumping small amounts of fluids within an ophthalmic device are also in the scope with the present disclosure. The mechanical membrane based system is an example but direct utilization of Electrowetting on dielectrics may provide other alternatives. For example, in still further embodiments, micro electro mechanical systems (MEMS) may also provide pumping functions by compressing fluid samples or imparting impulse upon fluid samples.

Figure 9:
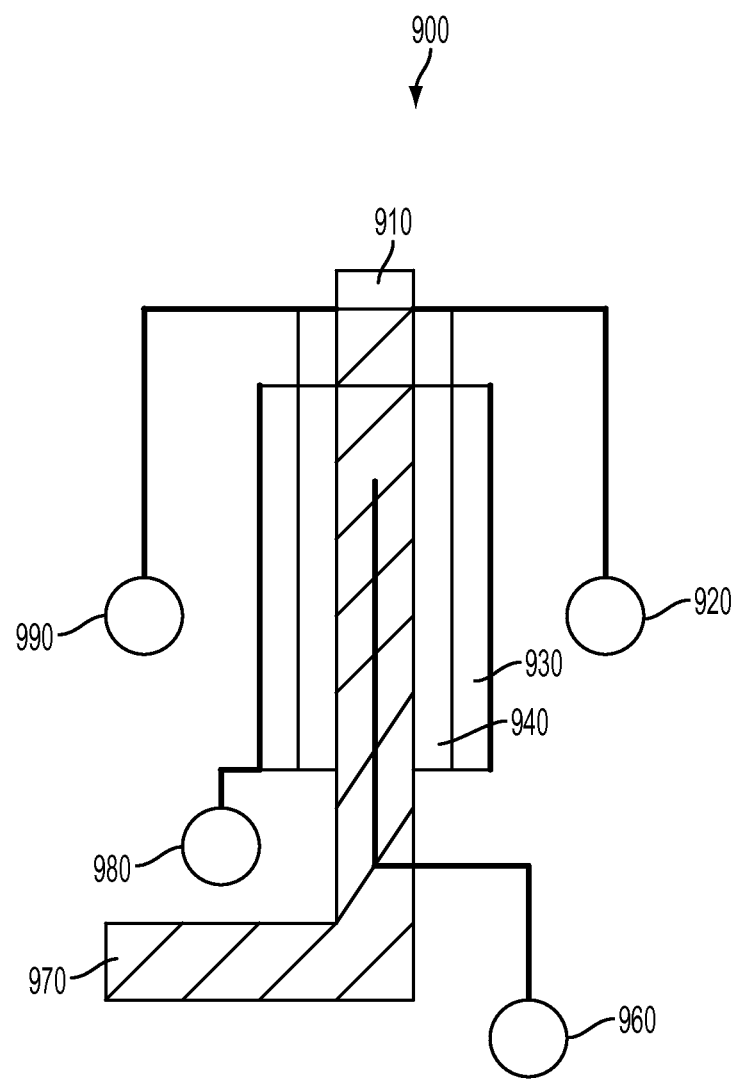
FIG. 9 illustrates a schematic design of an exemplary artificial pore 900 for an energized ophthalmic device capable of receiving a fluid sample into a Microfluidic Analytical System.

Energized Artificial Pores for Control of the Introduction of Fluids into Ophthalmic Devices Referring now to FIG. 9, a schematic design of an exemplary artificial pore 900 for an energized ophthalmic device capable of receiving a fluid sample into a microfluidic component is depicted. A sample fluid may reside in a region schematically demonstrated above pore access 910. In the operation of the artificial pore 900, at desired times the fluid may be allowed to flow from that region and into and ultimately through a fluid path channel 970. There may be numerous manners to control the flow of fluids through the channel including mechanical based mechanisms that may constrict or eliminate the cross sectional profile of the fluid path channel 970 in regions that may block flow.

In the present example, Electrowetting on dielectric effects may be used to create a repellant region in the pore access 910 region. A treated or formed surface 940 to be hydrophobic in nature may decrease the ability of hydrophilic or polar solvents to transverse the pore into fluid path channel 970. An electrode 960 may interact with fluids as they enter the pore region. A corresponding electrode 930 may also be located around the hydrophobic surface. This electrode 930 may be connected electrically To allow for the application of an electrical field, across electrodes 960 and 980, the surface wetting characteristic of the hydrophobic surface 940 may be altered to better allow flow through the region.

In some embodiments, an additional feature may be added to the artificial pore 900 to allow for the non-energized blocking of fluids preventing them from flowing through the pore access 910. This may be particularly useful when a device including the artificial pore 900 is in an initial storage after being produced. For example, the pore access 910 may be a thin film metal blocking feature. The film metal blocking feature may be connected through interconnect features 920 and 990. It may be possible that upon removal of the device containing the artificial pore 900 from a storage, that an activation signal may be communicated and received by the ophthalmic device. In some embodiments, when the ophthalmic device is ready to receive fluid samples for the first time, it may provide an electric potential across the metal interconnects 920 and 990 in such a manner that the current flow may be directed across the thin metal film 910. In some embodiments, this current flow may cause the thin metal film 910 to melt or evaporate, in either case exposing the underlying channel region 970 of the artificial pore 900.

Microfluidic Components in Stacked Integrated Die Embodiments

Reference has been made to electronic circuits making up part of the componentry of ophthalmic devices incorporating microfluidic elements. In some embodiments according to aspects of the disclosure, a single and/or multiple discrete electronic devices may be included as discrete chips, for example, in the ophthalmic Media Inserts. In other embodiments, the energized electronic elements can be included in the Media Insert in the form of Stacked Integrated Components. Accordingly and referring now to FIG. 10, a schematic diagram of an exemplary cross section of a Stacked Integrated Components implementing microfluidic elements incorporated within ophthalmic devices is depicted. In particular, the Media Insert may include numerous layers of different types which are encapsulated into contours consistent with the ophthalmic environment that they will occupy. In some embodiments, these Media Inserts with Stacked Integrated Component layers may assume the entire annular shape of the Media Insert. Alternatively in some cases, the Media Insert may be an annulus whereas the Stacked Integrated Components may occupy just a portion of the volume within the entire shape.

Figure 10:
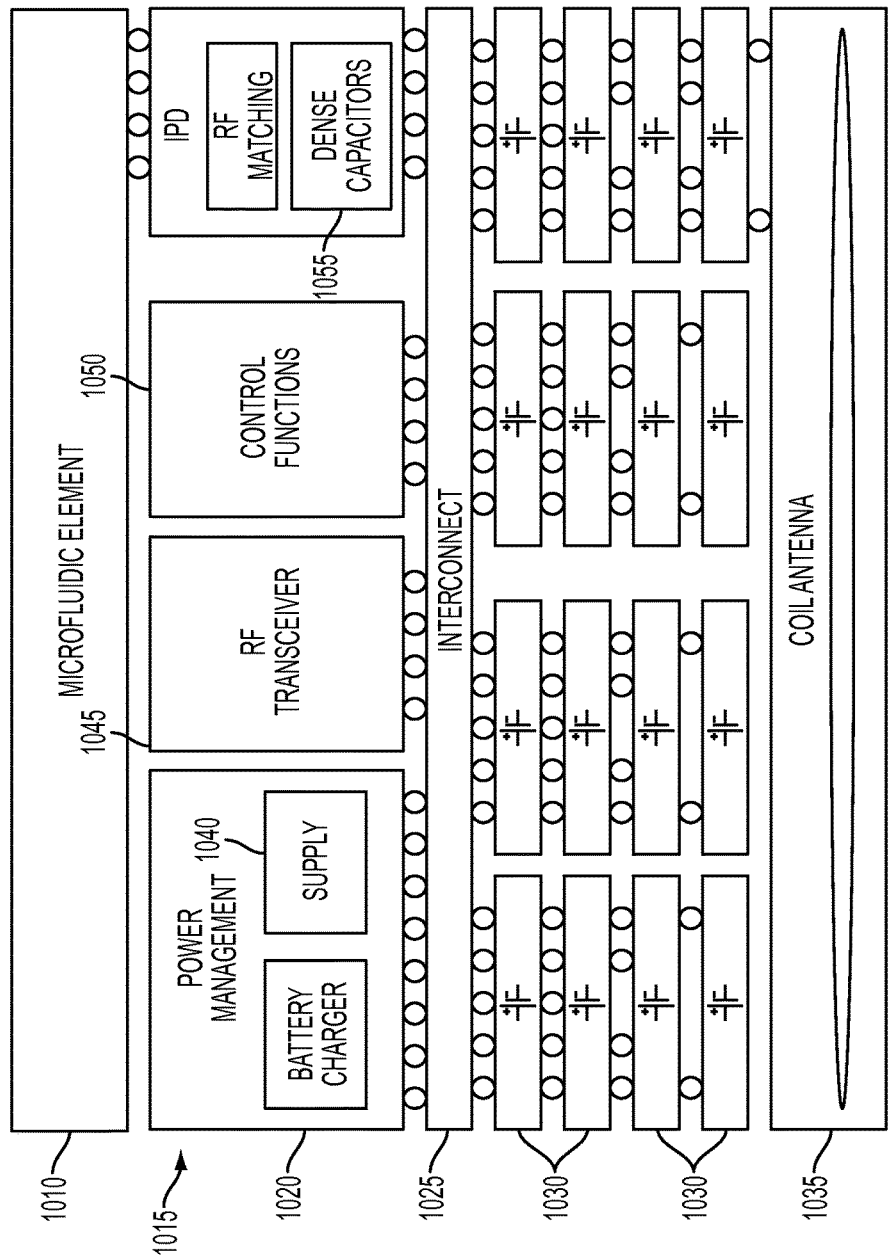
FIG. 10 illustrates a schematic diagram of an exemplary cross section of a stacked die integrated components implementing microfluidic elements incorporated within ophthalmic devices.

As shown in FIG. 10, there may be thin film batteries used to provide energization. In some embodiments, these thin film batteries may comprise one or more of the layers that can be stacked upon each other, in this case layers 1030 may represent the battery layers, with multiple components in the layers and interconnections therebetween.

In some embodiments, there may be additional interconnections between two layers that are stacked upon each other. In the state of the art there may be numerous manners to make these interconnections; however, as demonstrated the interconnection may be made through solder ball interconnections between the layers. In some embodiments only these connections may be required; however, in other cases the solder balls may contact other interconnection elements, as for example with a component having through layer vias.

In other layers of the Stacked Integrated Component Media Insert, a layer 1025 may be dedicated for the interconnections two or more of the various components in the interconnect layers. The interconnect layer 1025 may contain, vias and routing lines that can pass signals from various components to others. For example, interconnect layer 1025 may provide the various battery elements connections to a power management unit 1020 that may be present in a technology layer 1015. Other components in the technology layer 1015 can include, for example, a transceiver 1045, control components 1050 and the like. In addition, the interconnect layer 1025 may function to make connections between components in the technology layer 1015 as well as components outside the technology layer 1015; as may exist for example in the Integrated Passive Device 1055. There may be numerous manners for routing of electrical signals that may be supported by the presence of dedicated interconnect layers such as interconnect layer 1025.

In some embodiments, the technology layer 1015, like other layer components, may be included as multiple layers as these features represent a diversity of technology options that may be included in Media Inserts. In some embodiments, one of the layers may include CMOS, BiCMOS, Bipolar, or memory based technologies whereas the other layer may include a different technology. Alternatively, the two layers may represent different technology families within a same overall family; as for example one layer may include electronic elements produced using a 0.5 micron CMOS technology and another layer may include elements produced using a 20 nanometer CMOS technology. It may be apparent that many other combinations of various electronic technology types would be consistent within the art described herein.

In some embodiments, the Media Insert may include locations for electrical interconnections to components outside the insert. In other examples, however, the Media Insert may also include an interconnection to external components in a wireless manner. In such eases, the use of antennas in an antenna layer 1035 may provide exemplary manners of wireless communication. In many cases, such an antenna layer 1035 may be located, for example, on the top or bottom of the stacked integrated component device within the Media Insert.

In some of the embodiments discussed herein, the battery elements 1030 may be included as elements in at least one of the stacked layers themselves. It may be noted as well that other embodiments may be possible where the battery elements 1030 are located externally to the stacked integrated component layers. Still further diversity in embodiments may derive from the fact that a separate battery or other energization component may also exist within the Media Insert, or alternatively these separate energization components may also be located externally to the Media Insert.

A microfluidic element 1010 may be included in a Stacked Integrated Component architecture. In some embodiments, the microfluidic element 1010 component may be attached as a portion of a layer. In other embodiments, the entire microfluidic element 1010 may also comprise a similarly shaped component as the other Stacked Integrated Components. The various diversity of types of microfluidic elements 1010 that have been discussed herein may be consistent with a Stacked Integrated Component Device, where other features such as pumps, pores and the like are either a portion of a layer or alternatively attached either to the microfluidic cell or the layer that it attaches to.

Control Systems for Ophthalmic Devices with Integrated Microfluidic Components

Figure 11:
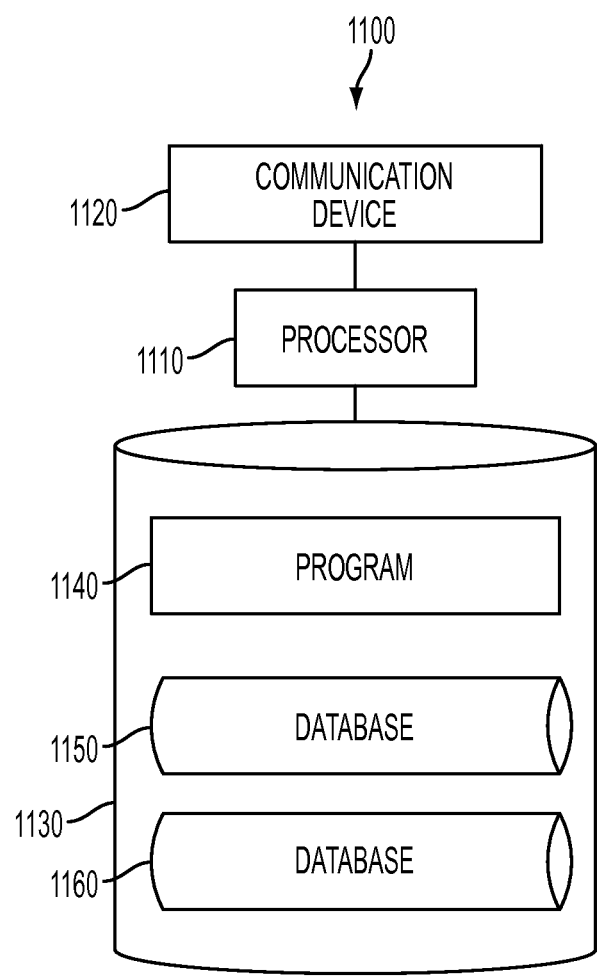
FIG. 11 illustrates a schematic diagram of a processor that may be used to implement some aspects of the present disclosure.

Referring now to FIG. 11 a controller 1100 is illustrated that may be used in some embodiments of the present disclosure. The controller 1100 can include one or more processors 1110, which may include one or more processor components coupled to a communication device 1120. In some embodiments, a controller 1100 can be used to transmit energy to the Energy Source placed in the ophthalmic lens.

The processors 1110 are coupled to a communication device configured to communicate energy via a communication channel. The communication device may be used to electronically communicate with components within the ophthalmic insert within the ophthalmic device. The communication device 1120 may also be used to communicate, for example, with one or more controller apparatus or programming/interface device components.

The processor 1110 is also in communication with a storage device 1130. The storage device 1130 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 1130 can store a program 1140 for controlling the processor 1110. The processor 1110 performs instructions of a software program 1140, and thereby operates in accordance with the present invention. For example, the processor 1110 may receive information descriptive of Media Insert placement, component placement, and the like. The storage device 1130 can also store ophthalmic related data in one or more databases 1150 and 1160. The database may include, for example, customized Media Insert designs, predetermined ocular fluid sample measurement thresholds, metrology data, and specific control sequences for controlling energy to and from a Media Insert. The database may also include parameters and controlling algorithms for the control of microfluidic analysis components that may reside in the ophthalmic device as well as data that result from their action. In some embodiments, that data may be ultimately communicated to an external reception device.

Figure 12:
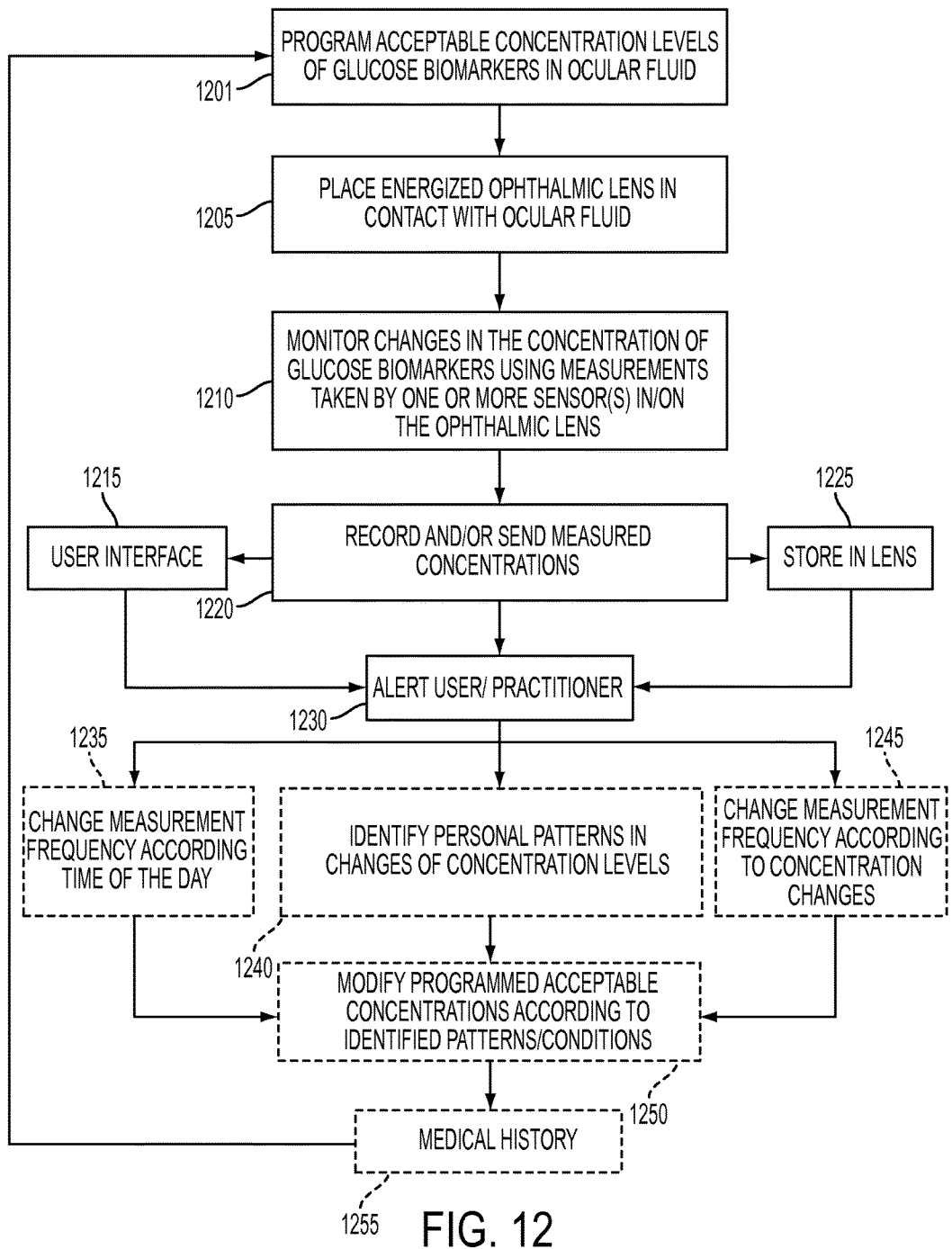
FIG. 12 illustrates exemplary method steps that may be used to monitor glucose levels of a user wearing the ophthalmic lens according to aspects of the present disclosure.

Referring now to FIG. 12, exemplary method steps that may be used to monitor glucose levels of a user wearing the ophthalmic lens according to aspects of the present disclosure are illustrated. At step 1201, thresholds values can be programmed into a software program. According to aspects of the present disclosure, threshold values can include, for example, acceptable levels for the concentration of glucose biomarkers in ocular fluid. The use of other biomarkers used to monitor different conditions such as depression, high blood pressure, and the such, are also within the inventive scope of aspects of the present disclosure. In addition, depending on whether the ocular fluid sample targeted is, for example, tear fluid or an interstitial fluid, the preprogrammed levels can be different. The program may be stored and executed using one or both a processor forming part of the Media Insert of the ophthalmic device and an exterior device in communication with the processor of the Media Insert. An exterior device may include a smart phone device, a PC, an ophthalmic device user interface, and the such, and can be configured to include executable code useful to monitor properties of ocular fluid samples. Ocular fluid properties can be measured by one or more sensors contained in the ophthalmic device. Sensors may include electrochemical sensors and/or photometric sensors. In an exemplary embodiment, the sensor analysis step may relate to a photometric sensing of glucose concentration based on a fluorescence sensor typology. In another example, the sensor may detect the presence of reaction products from a glucose oxidase interaction with portions of the analyte sensor and the fluid sample.

At step 1205, the ophthalmic device including a microfluidic system may be placed in contact with a portion of the anterior ocular surface of the eye and worn by a user. In some embodiments, the ophthalmic device can be in a form of an energized contact lens and the step may be achieved when the contact lens is placed on the eye surface. In other embodiments, the ophthalmic device may be, for example, in the form of an intraocular lens or a punctal plug, and still include aspects of the microfluidic analytical system described in the present disclosure. Although the ophthalmic device is described throughout the specification in singular form, it will be understood by one skilled in the art that two ophthalmic devices (e.g. contact lenses), one placed on each eye, may function together to provide functionality aspects of the present disclosure.

At step 1210, concentration changes of biomarkers can be monitored using the one or more sensors. The monitoring of the biomarkers may occur at a predetermined frequency or upon demand through a user interface and/or an activation sensor in the ophthalmic device. Biomarkers can include those correlated to glucose levels, depression, blood pressure and the such. At step 1220, the processor of the ophthalmic device can record the measured property/condition from a sample of ocular fluid. In some embodiments, the processor of the ophthalmic device may store it and/or send it to one or more device(s) in communication with the ophthalmic device. At step 1215, the value recorded can be stored and analyzed in the user interface in communication with the ophthalmic lens, and/or, at step 1225, the analysis and recording can take place in the ophthalmic device.

At step 1230, one or both the ophthalmic device and the user interface can alert the user, and/or a practitioner, of the measured concentration. The alert can be programmed to occur when the levels measured are outside the predetermined threshold values programmed, received and/or calculated by the ophthalmic device. In addition in some embodiments, the data and alerts may be analyzed to perform one or more steps of: a) change measurement frequency according to the time of the day, b) identify personal patters in the changes of concentration levels measures, and c) change the measurement frequency according to the changes in concentrations measured. At step 1235, the time of the day may change the frequency of measurements. For example, if the ophthalmic device is one that would remain in the eye during sleep, the number of measurements during 10 pm and 6 am can decrease or stop. Similarly, during lunch and dinner times the frequency may increase to detect changes due to the food consumption of the user. At step 1240, patterns in changes of the concentration levels may be identified by the system. Using the identified patterns, the system may alert the user of causes and/or, at step 1245, change the frequency according to the identified changes so that the system is more alert during critical identified conditions. Critical conditions can include events that would trigger a significant increase or decrease in glucose levels. Events can include, for example, holiday dates, exercise, location, time of the day, consumption of medicaments and the like.

In some embodiments, at step 1250, the originally programmed values may be customized, periodically or in real time, according to identified patterns/conditions. This ability may allow the system to increase its effectiveness by eliminating false alarms and increasing sensitivity at a critical condition. Effectiveness can promote user participation with the system thereby maximizing the benefits of the ophthalmic device and thereby providing a safe monitoring system. At step 1255, data relating to the user including, for example, the identified patterns, measurements, and/or preferences may become part of the medical history of the user. Medical history may be stored securely by encrypting the data and/or restricting its access.

Figure 13:
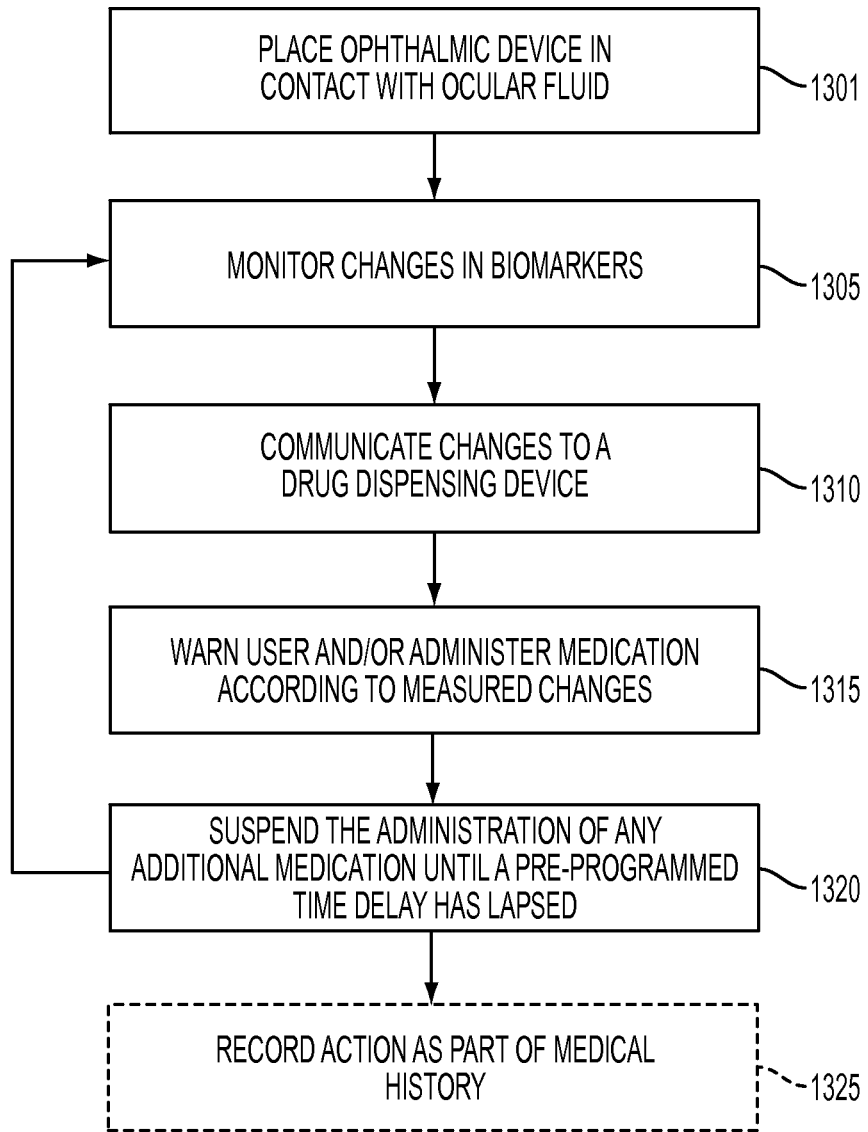
FIG. 13 illustrates exemplary method steps that may be used to treat the glucose levels of a user wearing the ophthalmic lens according to aspects of the present disclosure.

Referring now to FIG. 13, exemplary method steps that may be used to treat the glucose levels of a user wearing the ophthalmic lens according to aspects of the present disclosure are illustrated. At step 1301, an ophthalmic device including a microfluidic analytical system is placed in contact with ocular fluid. In some embodiments, the ophthalmic device can be in a form of an energized contact lens and the step may be achieved when the contact lens is placed on the eye surface. In other embodiments, the ophthalmic device may be, for example, in the form of an intraocular lens or a punctal plug, and still include aspects of the microfluidic analytical system described in the present disclosure.

At step 1305, changes in biomarkers in the ocular fluid can be monitored. Methods of monitoring the biomarker changes can include, for example, steps illustrated in FIG. 12. At step 1310, measured changes can be communicated in real time to a medicament-dispensing device in direct or indirect communication with the ophthalmic device. Although the changes in concentration of the monitored biomarkers in ocular fluid may include a time delay in relation to the concentration changes in the bloodstream of the user, upon detection, at step 1315 the medicament-dispensing device may administer a medicament capable of lowering or raising concentrations to a normal level. For example, glucose levels may be monitored and treated when they are outside a normal level. Continuous monitoring can prevent uncontrolled blood sugar levels which can damage the vessels that supply blood to important organs, like the heart, kidneys, eyes, and nerves. Because an individual whose glucose levels may reach a level that exposes him/her to said risks may feel ok, aspects of the present disclosure can help take action upon early detection of the condition. Early detection may not only bring back levels to a normal conditions and/or make the user aware, but additionally prevent the more dramatic and permanent consequences including, for example, a heart attack or stroke, kidney failure, and blindness which have been known to occur when abnormal glucose levels are left untreated.

In addition, in some embodiments the medicament-administering device may send an alert to the user through its interface or using component of the ophthalmic device. For example, in some ophthalmic device embodiments the Media Insert may include a light projection system, such as one or more LEDs, capable of sending a signal to the user.

Subsequently at step 1320, any further drug administering can be suspended to prevent overdosing of the system due to the time delay of the effect of the drug and the effect to be reflected in the tear fluid. For example, the medicament may require 10-30 minutes to counteract the abnormal level, and upon its effect, may take another 20 minutes to equalize concentrations in tear fluid. Consequently, programmed algorithms capable of correlating the condition, time delay, and appropriate subsequent dosing of medicaments can be programmed in the system to function safely. At step 1325, data relating to one or both the measured conditions and the medicament administration to the user may be stored and used as part of a treatment and/or medical history of the user.

Specific examples and method steps have been described to explain and enable different aspects of the present invention. These method steps and examples are for illustration purposes and are not intended to limit the scope of the claims in any manner. Accordingly, the description is intended to embrace all embodiments that may be apparent to those skilled in the art.

The invention claimed is:

1. An ophthalmic device, including an ocular fluid analysis system, comprising:
   an ophthalmic device body;
   a media insert encapsulated within the ophthalmic device body, wherein the media insert comprises a first annular insert piece attached to and sealed together with a second annular insert piece to form an annular shaped insert having an annular cavity between the first annular insert piece and the second annular insert piece,
   an energy source within the cavity and configured to provide energy to the ocular fluid analysis system,
   a microfluidic analytical system within the cavity and in electrical communication with the energy source, wherein the microfluidic analytical system comprises a micro-channel for receiving and transporting fluid and is configured operatively to measure one or more properties of an ocular fluid sample flowed through the micro-channel; and,
   a processor within the cavity and configured to execute a program including preprogrammed threshold values for one or more of the ocular fluid properties and to output a signal when the received measurements are outside the corresponding preprogrammed threshold values;
   the media insert further comprises an opening into the cavity that exposes the micro-channel of the microfluidic analytical system to a user's ocular fluid that is external to the ophthalmic device.

2. The ophthalmic device of claim 1, wherein:
   the outputted signal can cause the activation of a medicament administering device capable of administering a medicament based on outputted signal.

3. The ophthalmic device of claim 1, additionally comprising:
   an artificial pore controlling a fluid path leading to a microfluidic pump component.

4. The ophthalmic device of claim 3, wherein:
   the microfluidic pump component operates using electrowetting of dielectric principles.

5. The ophthalmic device of claim 3, wherein:
   the microfluidic pump component operates using electrophoresis principles.

6. The ophthalmic device of claim 1, wherein:
   the microfluidic analytical system operates to perform biochemical analysis of an ocular fluid sample in an interactive environment on a microchip sized wafer.

7. The ophthalmic device of claim 1, wherein:
   the ophthalmic device body is a hydrogel contact lens.

8. The ophthalmic device of claim 1, wherein:
   the preprogrammed threshold values are normal glucose concentration levels in an ocular fluid sample.

9. The ophthalmic device of claim 8, wherein:
   the ocular fluid sample is a tear fluid sample.

10. The ophthalmic device of claim 1, wherein the media insert has a circular peripheral edge with a diameter that is less than the diameter of the ophthalmic body and is positioned within the ophthalmic body such that the center of the media insert is aligned with the center of the ophthalmic body.

11. The ophthalmic device of claim 1, wherein the media insert is in direct contact with an anterior surface of the eye.

12. The ophthalmic device of claim 1, wherein the media insert is encapsulated in a semi-permeable membrane to selectively permit substances to penetrate or escape the media insert.

13. The ophthalmic device of claim 1, wherein the ocular fluid analysis system includes a pore and a pore control element connected to the microfluidic analytical system and configured to permit emission of monitored ocular fluid from the ophthalmic device.

* * * * *